United States Patent [19]

Williams et al.

[11] 4,027,161
[45] May 31, 1977

[54] MINIMIZING WAVE INTERFERENCE EFFECTS ON THE MEASUREMENT OF THIN FILMS HAVING SPECULAR SURFACES USING INFRARED RADIATION

[75] Inventors: Paul Williams; Jon Francis Pugh, both of Columbus, Ohio

[73] Assignee: Industrial Nucleonics Corporation, Columbus, Ohio

[22] Filed: Apr. 5, 1976

[21] Appl. No.: 673,534

[52] U.S. Cl. .............................. 250/339; 250/341; 250/353
[51] Int. Cl.² ...................................... G01J 1/00
[58] Field of Search .......... 250/338, 339, 340, 341, 250/353

[56] References Cited

UNITED STATES PATENTS

| | | | |
|---|---|---|---|
| 3,631,526 | 12/1971 | Brunton | 250/338 X |
| 3,793,524 | 2/1974 | Howarth | 250/339 |
| 3,854,044 | 12/1974 | Stay et al. | 250/338 |
| 3,863,071 | 1/1975 | Campanella | 250/339 |
| 3,870,884 | 3/1975 | Williams | 250/339 |

*Primary Examiner*—Davis L. Willis
*Attorney, Agent, or Firm*—C. Henry Peterson

[57] ABSTRACT

A property of a thin, infrared radiation-transmissive film of plastic or the like with specular surfaces is measured with substantial freedom from errors caused by wave interference effects, utilizing first and second infrared radiations having wavelengths selected so that one of the radiations is subject to greater absorption in the film material than the other radiation. Beams of each of the radiations are directed from a multiplicity of points as on the diffusively reflective inner surface of a sphere to a surface of the film at a broad spectrum of incidence angles so that the beams traverse a multiplicity of paths through the film constituting a broad spectrum of path lengths. Radiations leaving the film are intercepted and redirected from a multiplicity of points to a surface of the film at a broad spectrum of incidence angles so that the redirected radiations also traverse a multiplicity of paths through the film constituting a broad spectrum of path lengths. Each of the first and second radiations are detected with detecting means so arranged with respect to the directing and redirecting points that detected components of each radiation are added at substantially all possible phase angles and so that the components of each of the respective radiations at each of the possible phase angles approach equality of intensity as detected by the detecting means. A response produced is indicative of the film property as a function of the ratio of the detected intensities of the first and second infrared radiations.

54 Claims, 10 Drawing Figures

MINIMIZING WAVE INTERFERENCE EFFECTS ON THE MEASUREMENT OF THIN FILMS HAVING SPECULAR SURFACES USING INFRARED RADIATION

This invention relates to infrared radiation-gauging methods and apparatus which are particularly adapted for measuring a property of a very thin, infrared radiation-transmissive film, of plastic or other material, having specular surfaces. More specifically the invention relates to methods and apparatus whereby infrared radiations in at least two selected wavelength regions are directed and redirected onto one or both surfaces of the film from a multiplicity of points arranged so that radiation beams traverse a multiplicity of paths through the film constituting a broad spectrum of path lengths. Radiations are detected with detecting means so arranged with respect to the directing and redirecting points that components of each wavelength of radiation are detected at substantially all possible phase angles and so that the components of each of the respective wavelength radiations at each of the possible phase angles approach equality of intensity as detected by the detecting means. The production of a response indicative of the film property as a function of the ratio of the detected intensities of the respective wavelengths of radiation can thereby result in a measurement which exhibits substantially reduced errors due to wave interference effects.

The problems arising from the effects wave interference, or so-called channeled spectra, in very thin, transparent film measurements are set forth, together with general and specific solutions to the problems, in U.S. Pat. No. 3,631,526. This patent discloses and claims, inter alia, the technique of directing infrared radiation beams toward one surface of a film at a broad spectrum of incidence angles so that components of each beam are added at all possible phase angles. This technique is sound in principle, and the specifically disclosed methods and apparatus for implementing it can result in a substantial improvement in the performance of thin-film gauges.

However, the specifically disclosed methods and apparatus do not adequately take into account certain factors which may not allow the added components of each beam to be detected in such a manner that the components at each of the possible phase angles approach equality as detected. For example, as is well known the intensity of radiation from a point source, passing directly to and incident on the surface of a film at various incidence angles (angles of incidence), varies with the sine of the incidence angle. There is a similar intensity variation in the radiation incident on different portions of an elongated detector. Moreover, different portions of an extended detector may not exhibit equal responses to radiation of the same quality and intensity. As a result of such factors, the desired cancellation of interference effects is incomplete, resulting in measurement errors which can be of serious consequence in many thin film gauging applications.

The fact that prior art thin film gauging methods and apparatus do not properly re-collect or redirect radiations leaving the film after interacting with it through reflection and transmission modes has an essence resulted in a loss of information which is needed and should be utilized in order to effect correction of the interference errors. The present invention provides methods and apparatus which can substantially alleviate many of the difficulties encountered in the practical implementation of the prior art thin film guaging techniques.

In accordance with this invention, there is provided a method and apparatus for measuring a property of an infrared radiation-transmissive film having specular surfaces, comprising the steps of, and means for, generating first and second infrared radiations having wavelengths selected so that one of the radiations is subject to greater absorption in the film material than the other radiation, directing beams of each of the radiations from a multiplicity of points to a surface of the film at a broad spectrum of incidence angles so that the beams traverse a multiplicity of paths through the film constituting a broad spectrum of path lengths, intercepting radiations leaving the film and redirecting the intercepted radiations from a multiplicity of points to a surface of the film at a broad spectrum of incidence angles so that the redirected radiations also traverse a multiplicity of paths through the film constituting a broad spectrum of path lengths, detecting each of the first and second radiations with detecting means so arranged with respect to the directing and redirecting points that detected components of each radiation are added at substantially all possible phase angles and so that the components of each of the respective radiations at each of the possible phase angles approach equality of intensity as detected by the detecting means and producing a response indicative of the film property as a function of the ratio of the detected intensities of the first and second infrared radiations.

Where a substantial portion of the radiations incident on one surface of the film emerge from the opposite surface, the method may comprise, and means may be provided for, redirecting a major portion of the emergent radiations back to the opposite surface at a broad spectrum of incidence angles.

Typically the method comprises, and means are provided, for generating one of the first and second radiations as a narrow band of wavelengths subject to substantial absorption in the film material, and generating the other of the first and second radiations as a pair of narrow bands of wavelengths occupying spectral regions on either side of and closely adjacent to the narrow band of wavelengths, the radiations having said pair of adjacent wavelengths being substantially less subject to absorption in the film material than said one radiation.

Methods and means may be provided for locating minute infrared radiation reflective elements at the beam directing points, and illuminating the elements by an infrared radiation source which generates the first and second radiations whereby said beams incident on the surface of the film and traversing the paths through the film comprise infrared radiations reflected from the elements. The elements may be located in an enclosing configuration which substantially confines a surface area of the film.

Typically methods and means are provided for directing a primary beam of radiations from the source onto a primary reflector located within the enclosing configuration so that the reflecting elements at the beam directing points are illuminated by infrared radiations reflected from the primary reflector. The primary beam of radiations from the source are typically collimated by a collimator, and directed onto the primary reflector so that substantially all radiation from the source admitted within the enclosing configuration is reflected by the primary reflector.

Typically the enclosing configuration comprises a surface of revolution such as a hemisphere, and the elements are located on the surface of revolution. A portion of the area of the film confined by the surface of revolution may be masked off to block the passage of radiation to the surface of the film except in a narrow, elongated area thereof.

Infrared radiation reflective elements may also be located at the beam redirecting points. The reflective elements may be located on both sides of the film to form enclosing configurations which confine an area of the film on both sides thereof. The radiations may be detected with a detecting means so arranged that radiation cannot pass from the source to the detecting means without interacting with one of the radiation reflecting elements. Again each of the enclosing configurations may comprise a surface of revolution such as a hemisphere.

A method and means may be provided for directing a primary beam of radiations from the source through the film from one side thereof to illuminate reflective elements on the opposite side of the film.

Typically the beam directing points are located on a continuous material surface, and the radiation reflective elements are formed as an integral portion of the material surface. The continuous material surface may be formed of a material such as aluminum which is highly reflective to infrared radiation. The radiation reflective elements may be formed by sandblasting the surface of the aluminum.

The invention further provides apparatus for measuring a property of sheet material, comprising a radiation source for generating infrared radiation having a wavelength subject to absorption in the sheet material, means for directing beams of the radiation from a multiplicity of points to a surface of the sheet material at a broad spectrum of incidence angles, means for intercepting radiation leaving the sheet material and for redirecting the intercepted radiation to a surface of the sheet material, said directing and redirecting means comprising reflective surface elements forming an enclosing configuration which substantially confines a surface area of the sheet material, a primary reflector located within the enclosing configuration, means for directing a primary beam of radiation from the source onto the primary reflector so that the reflective surface elements at the beam-directing points are illuminated by infrared radiation reflected from the primary reflector, means for detecting a portion of the radiations which have left the sheet material, and means for producing a response indicative of the sheet property as a function of the detected radiation.

Typically the beam-directing points may be located on a diffusively reflective, continuous material surface and the primary reflector may have a specular surface. Alternatively, at least for some applications the continuous material surface may be a specularly reflective surface and the primary reflector may have a diffusively reflective surface.

The objects of the present invention are to provide methods and means for measuring thin, infrared radiation-transmissive film with increased independence of interference effects as a result of reflections from the specular surfaces of the film, to provide methods and means for achieving higher signal-to-noise ratios in the measurements of such films, to provide thin film-measuring methods and means which will allow a wider range of thicknesses of film to be gauged with a single geometric and signal-processing arrangement, to provide thin film measuring methods and apparatus which permit the use of narrower bands of wavelengths without encountering intolerable wave interference effects, and to provide a novel geometric arrangement of apparatus for improving the performance of infrared radiation gauges adapted for the measurement of sheet materials generally.

Other objects and advantages of the present invention will become apparent in the following detailed description of some typical procedures and apparatus for practicing the present invention, taken in conjunction with the appended drawings, in which.

Figure 1:
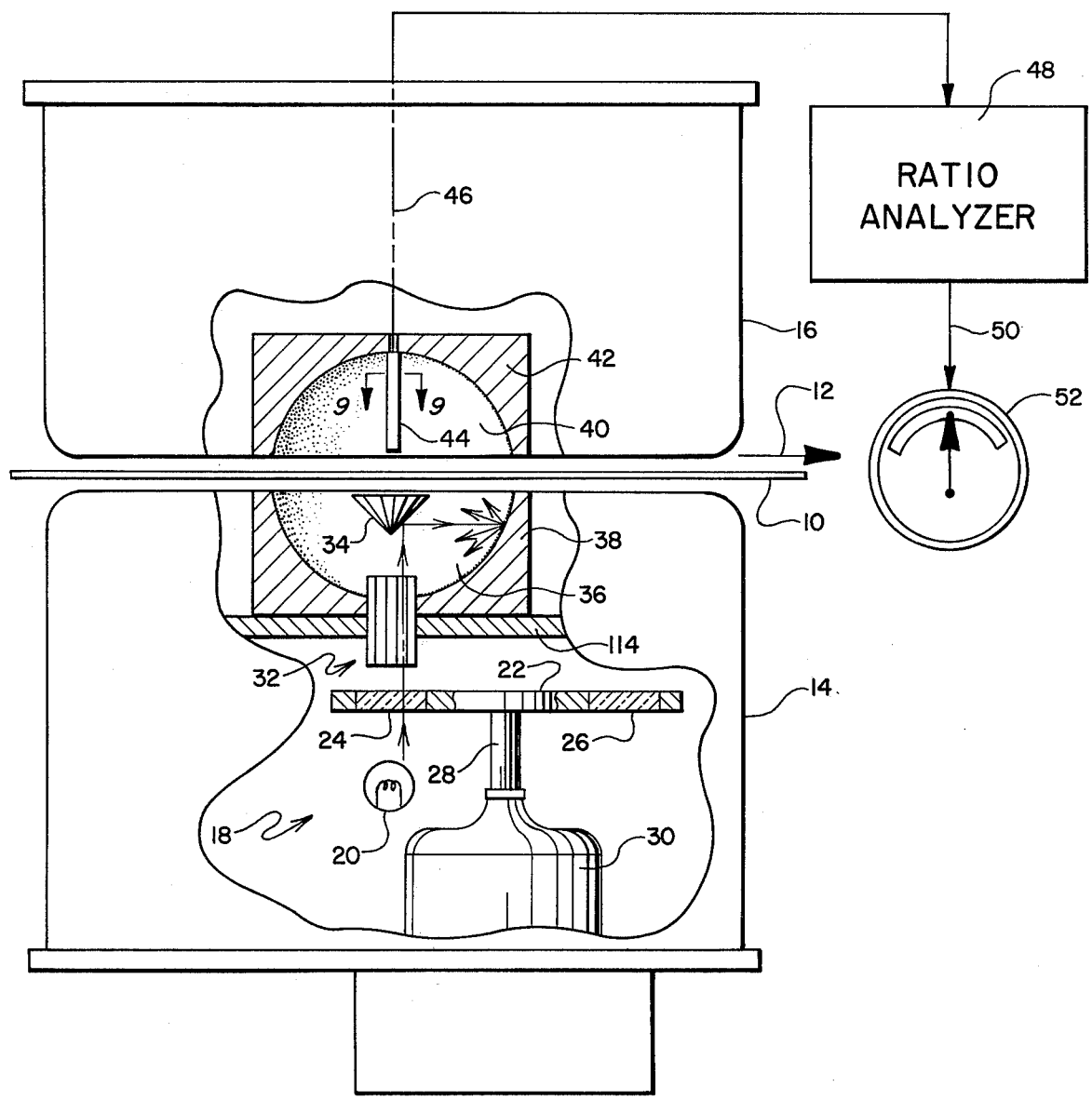
FIG. 1 is a generally schematic, partially sectional view of a measuring instrument including radiation source and detector heads for measuring a property of a thin film in accordance with the present invention.

Referring to FIG. 1, the numeral 10 indicates the edge view of a thin, infrared radiation-transmissive film having specular surfaces. Typically film 10 may have a thickness considerably less than one mil. It may be a film produced by a cast film-making apparatus, and may be traveling as indicated by the arrow 12 in a direction through or away from the film-casting machine. Typically, a signal from the film-measuring apparatus herein disclosed may be used to automatically control or regulate a property of the film such as its thickness, weight per unit area or composition by controlling and adjustable parameter of the film-casting machine.

The numeral 14 designates the outline of an infrared radiation source housing and the numeral 16 designates the outline of an infrared radiation detector housing. These are conventional housing, typically mounted on a conventional traversing structure (not shown), which allows the source and detector housings 14 and 16 to traverse back and forth across the width of the traveling film, in order to gauge the film property at any point across the width.

Within source housing 14 is a conventional radiation source arrangement indicated generally by the numeral 18. The radiation source arrangement typically includes means for generating first and second infrared radiations wavelengths selected so that one of the radiations is subject to greater absorption in the material of film 10 than the other radiation. For special applications, arrangements can be made to generate, or at least to effectively use, radiations in more than two wavelength regions.

The source arrangement shown includes a conventional lamp 20 and a conventional chopper and filter system. It includes a chopper disc 22 having mounted therein a pair of filters 24 and 26. The chopper disc 22 is driven through shaft 28 by a synchronous motor 30. As motor 30 rotates disc 22, filters 24 and 26 are alternately positioned between lamp 20 and a collimator 32. The filters 24 and 26 are thus enabled to send through collimator 32 time-alternating infrared radiations of effectively different wavelengths. Filter 24 selects and passes to collimator 32 an infrared radiation in a band of wavelengths which are subject to greater absorption in the material of film 10 than the radiation selected and passed to collimator 32 by filter 26.

The collimated beams of radiations passing through collimator 32 are thereby directed onto a primary reflector 34 in the shape of a cone. The apex of the cone is directed toward collimator 32, and the lateral surface of the cone presented to the collimator has a highly polished finish. Typically the primary reflector 34 is constructed of solid aluminum having a highly polished mirror surface presented to collimator 32. The polished surface of the cone is inclined at an angle of 45° to the axis of collimator 32, so that radiation is reflected from the surface of the cone at an angle of about 90° with respect to the axis of the collimator 32.

The radiation reflected from primary reflector 34 illuminates at least a substantial area of the inner walls of a cavity 36. Cavity 36 is hollowed out of right circular cylindrical segment 38 of solid aluminum. From the inner wall defining cavity 36, beams of radiation are directed from a multiplicity of points to the bottom surface of film 10 at a broad spectrum of incidence angles so that the beams traverse a multiplicity of paths through the film constituting a broad spectrum of path lengths.

Adjacent to the opposite surface of film 10 is a second cavity 40 which matches cavity 36 and is hollowed out of a second aluminum segment 42.

For the most part, radiations passing through film 10 and leaving the film on the opposite side are intercepted by the inner wall of cavity 40. Radiations reflected from film 10 and leaving the film from the bottom surface thereof are intercepted by the wall of cavity 36. The radiations leaving the film and so intercepted are redirected from a multiplicity of points on the inner surface of cavity 36 or cavity 40 to the top or the bottom surface of the film at a broad spectrum of incidence angles so that the redirected radiations also traverse a multiplicity of paths through the film constituting a broad spectrum of path lengths.

Mounted in cavity 40 is a detecting means indicated generally at 44 for detecting each of the first and second radiations selected by filters 24 and 26. The detecting means is so arranged with respect to the directing and redirecting points on the inner walls forming cavities 36 and 40 that detected components of each radiation are added at substantially all possible phase angles and so that the components of each of the respective radiations at each of the possible phase angles approach equality of intensity as detected by the detecting means. Detecting means 44 is schematically shown to be connected via line 46 to a conventional ratio analyzer 48. Ratio analyzer 48 produces a response indicative of the film property as a function of the ratio of the detected intensities of the first and second infrared radiations. This response is transmitted via line 50 to a suitable instrument 52 which may be a visual indicator and/or recording device, and may incorporate or be associated with an arrangement for automatically controlling or regulating the film producing machine (not shown) in order to maintain the measured property of film 10 at a desired value.

Figure 2:
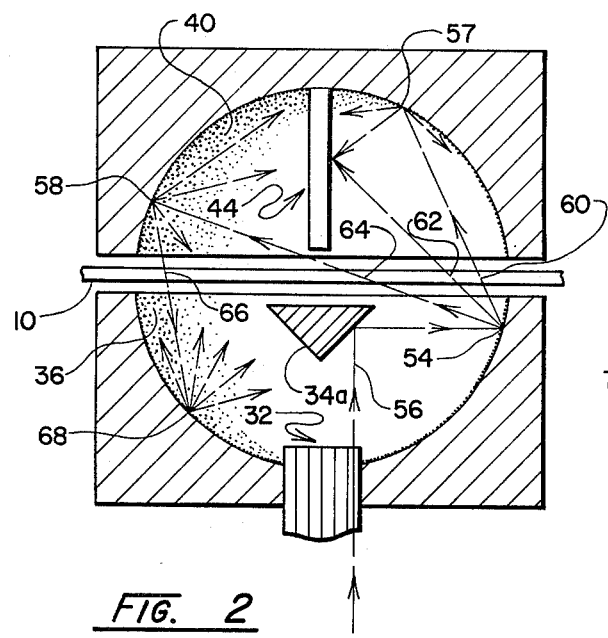
FIG. 2 is a schematic, sectional view of a modified portion of FIG. 1, showing typical radiation beam paths through the film 10, whose thickness is greatly exaggerated.

FIG. 2 shows an enlargement of the members forming cavities 36 and 40 and the parts contained therein. The thickness of film 10 is greatly exaggerated to show the interaction of some typical transmitted radiation beams with the film and with the inner surfaces of the cavities. The effects of refraction on the radiation beams are not taken into account, since they do not have any practical affect on the overall arrangement. FIG. 2 differs from FIG. 1 in that a solid metal prism or wedge 34a is shown in place of the cone 34 of FIG. 1 which constitutes the primary reflector. The wedge 34a is in the shape of a triangular, solid aluminum prism, with two highly polished faces in line with the openings in collimator 32. The cone is replaced by the prism in order to measure a narrow elongated area of film 10, as will be more fully described hereinafter.

The cavities 36 and 40 have diffusing surfaces formed by sandblasting the aluminum, although other methods, some of which are described in U.S. Pat. No. 3,222,522, can also be used. The sandblasting produces a vast number of small pits and projections in the surface of the aluminum, forming minute infrared radiation reflective elements at a great multiplicity of beam directing points such as point 54. These minute reflective elements are illuminated by the infrared radiation source, as shown by the ray 56 passing through collimator 32 and reflected from one of the polished surfaces wedge 34a onto reflective elements at point 54.

As illustrated in FIG. 2, and as described above, the minute infrared radiation reflective elements are located on a continuous material surface, and are formed as an integral portion of the material surface, but it will be apparent that the elements could be formed and mounted in different ways. As shown, the elements are located in an enclosing configuration which substantially confines the surface area of the film which is instantaneously located across the mouth of the cavity 36. Since the primary reflector wedge 34a is larger than the total cross section of the radiation beams passing through collimator 32, substantially all radiation from the source admitted within the enclosing configuration is reflected by the primary reflector.

Typically, the enclosing configuration is a surface of revolution. As illustrated, this surface of revolution is a hemisphere, but it is apparent that other designs utilizing paraboloidal, ellipsoidal, hyperboloidal or other surfaces of revolution may be employed in appropriately designed configurations compatible with the shape of an associated primary reflector such as reflector 34a.

In the apparatus of FIGS. 1 and 2, radiation-reflective elements are located on both sides of the film to form enclosing configurations which confine an area of the film on both sides thereof. For example, radiation-reflective elements are located at points 57 and 58 on the opposite side of the film.

As shown by the rays in FIG. 2, beams of radiation from a multiplicity of points such as point 54 are directed onto the surface of the film at a broad spectrum of incidence angles so that the beams traverse a multiplicity of paths through the film constituting a braod spectrum of path lengths. For example a beam from one of the minute reflectors at point 54 follows a path 60 after impinging on the film at a small incidence angle whereby the length of the path 60 through the film is not much greater than the film thickness. A beam from another reflector is incident on the film at an intermediate incidence angle and traverses a longer path 62 through the film. A beam from still another reflector is incident on the film at a large incidence angle, and traverses a still longer path 64 through the film.

It is noted that the beam of radiation which traverses path 62 through film 10 is directly detected by the detector means 44. The beam which traverses path 60 through the film is intercepted by reflectors at point 57 and diffused, with a portion of the diffused radiation being detected by the detector and the rest redirected in other directions. The beam which traverses path 64 through the film is intercepted by reflectors at point 58 and redirected to a surface of the film at a broad spectrum of incidence angles so that the redirected radiations also traverse a multiplicity of paths through the film constituting a broad spectrum of path lengths. One redirected beam traverses a path 66 through the film and is redirected a second time from a point 68 on the first side of the film.

Figure 3:
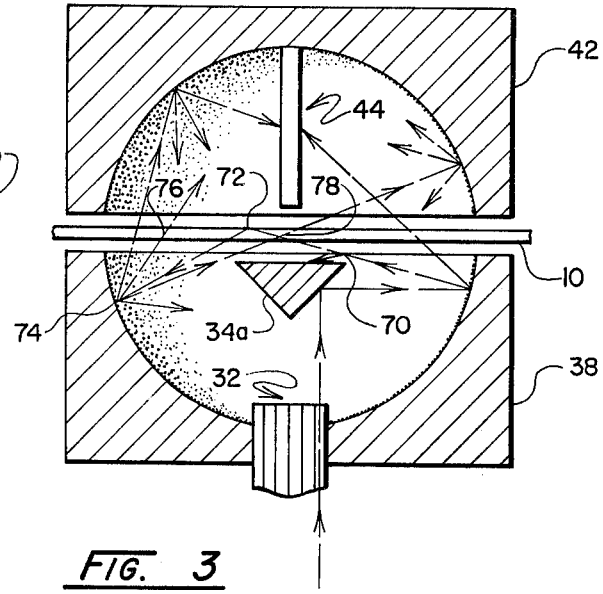
FIG. 3 is like FIG. 2, but modified to show additional typical beam paths.

Whereas the rays passing through the film from one side thereof are shown to leave the film on its opposite side in FIG. 2, as shown in FIG. 3 it is apparent that radiation beams entering the film from one side of the film may also leave the film on the same side at which they entered. For example, at 70 it is seen that a ray incident on the bottom surface of the film may be partially reflected from the bottom surface, thereby leaving the film via one reflection path. A beam of radiation may enter the film through the bottom surface and be reflected as at 72 from the top surface of the film back through the film, thereby leaving the film via another reflection path. Such reflected rays are intercepted by reflectors as at point 74 and redirected so that they traverse paths of different lengths in the film as shown at 76 and 78.

While only a few directing and redirecting points with their associated reflective elements can be shown in FIGS. 2 and 3, it is apparent that an almost infinite number of minute reflectors are formed at an almost infinite number of directing and redirecting points on the hemispherical surfaces disclosed, and that each of the first and second radiations are detected in such a way that detected components of each radiation are added at substantially all possible phase angles and so that the components of each of the respective radiations at each of the possible phase angles approach equality of intensity as detected.

As shown in FIG. 2, a substantial portion of the radiations incident on the one (bottom) surface of the film emerge from the opposite (top) surface. A major portion of the emergent radiations are intercepted by the reflectors as at point 58 and directed back to the opposite (top) surface at a broad spectrum of incidence angles. Ultimately, the radiations are detected by the detector means 44 located above the opposite surface.

Figure 4:
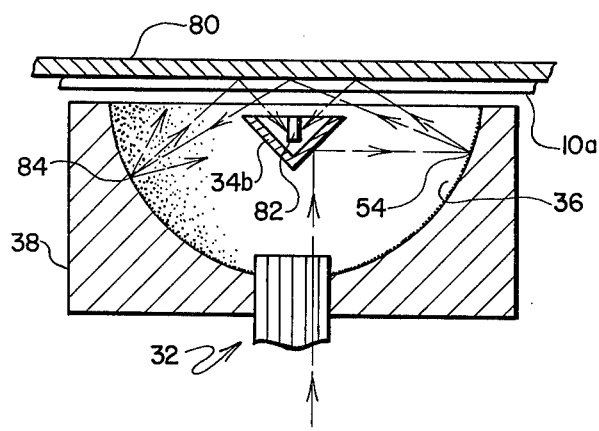
FIG. 4 shows a modification of the apparatus of FIG. 2 or FIG. 3 adapted for measurement of a film, such as film deposited on a substrate, from one side thereof.

FIG. 4, however, shows an arrangement for measuring the thickness of a film from only one side. Such an arrangement is useful, for example, where the measured film 10a is formed on a substrate 80. The illustrative apparatus again utilizes a hemispherical cavity 36 formed in an aluminum body 38 and a collimator 32. The primary reflector 34b comprises a metal cone with polished surfaces similar to that shown at 34 in FIG. 1. However, in this case the cone is typically hollowed out on the back side to accommodate a detector 82. Detector 82 is connected to a ratio analyzer, and if desired, to a readout and control device in a manner similar to that of the arrangement shown in FIG. 1. Radiation beams are directed, as from point 54, to the surface of the film at a broad spectrum of incidence angles, so that the beams traverse a multiplicity of paths through the film constituting a broad spectrum of path lengths. Radiations reflected from the film, for example at the interface between the film 10a and the substrate 80, and not intercepted by detector 82 and/or cone 34b, are intercepted by reflective elements as at point 84 on the hemispherical surface and redirected to the surface of the film at a broad spectrum of incidence angles so that the redirected radiations also traverse a multiplicity of paths through the film constituting a broad spectrum of path lengths. In other respects, the arrangement of FIG. 4 functions in a manner similar to the arrangement of FIGS. 1 to 3.

In the arrangements of FIGS. 1 to 4, the primary beams of radiation from the source are directed onto a primary reflector so that the reflecting elements at the beam directing points are illuminated by infrared radiation reflected from the primary reflector. Also, the collimator and primary reflector are arranged so that substantially all radiation from the source admitted within the enclosing configuration is reflected by the primary reflector. In other arrangements such as those depicted schematically in FIGS. 5 and 6, a primary beam of radiation from the source is directed through the film from one side thereof to illuminate reflective elements at beam directing points on the opposite side of the film.

Figure 5:
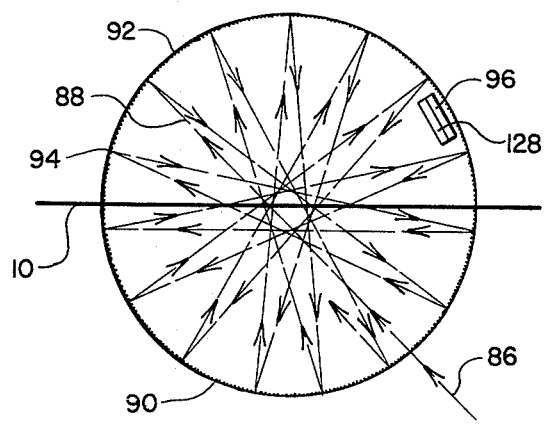
FIG. 5 is a schematic diagram showing the principles of a possible modification of the apparatus of FIG. 2 or FIG. 3, illustrating in particular typical ray paths in an apparatus so modified.

As depicted in FIG. 5, the primary beam of radiation represented by arrow 86 is directed along a path 88 which is displaced a suitable distance from the center of the spherical cavity enclosed by the two hemispheres indicated at 90 and 92. The beam after passing through film 10 is incident on reflectors as at 94 on the surface of hemisphere 92, and from there the radiation is directed to a surface of the film at a broad spectrum of incidence angles. For purposes of locating the path of the primary beam 88 and the detector shown at 96, the inner surface of the spherical cavity may be considered to be a specular surface, and only specularly reflected beams are shown in FIG. 5. The illustrated hypothetical specularly reflected beams pass through the film at a multiplicity of angles, and detector 96 is positioned out of the path of any radiation postulated to be transmitted to the detector via a preferred angular route. As a matter of fact, however, as shown the spherical cavity of FIG. 5 has diffusing inner surfaces similar to those of FIGS. 1 to 4, so that specular reflection from the inside surface forming the spherical cavity is substantially nonexistent. Accordingly, the arrangement of FIG. 5 may be enabled to approach the performance characteristics of the other previously described arrangements.

An arrangement which may be preferable to that of FIG. 5, however, is one in which the primary radiation beam 86a is directed into the spherical cavity in a beam parallel to the film 10. The radiation which first interacts with the film thereby constitutes radiation which has first interacted with at least one of the minute radiation reflecting elements, as at point 98, even though the film itself may contain minute scattering bodies which are able to scatter a substantial part of the "first pass" radiation.

Figure 7:
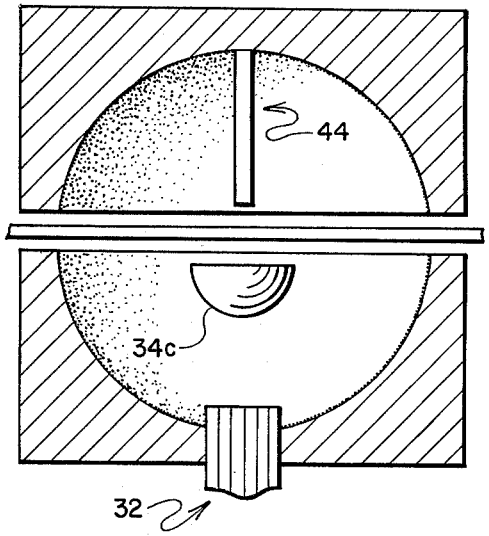
FIG. 7 is a schematic showing of another modification of apparatus according to the invention.
Figure 6:
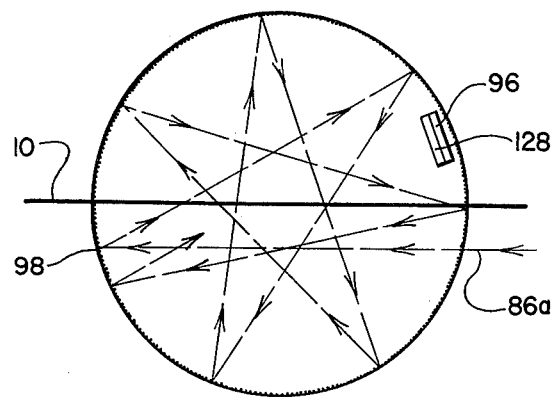
FIG. 6 is a schematic diagram similar to FIG. 5, showing in particular ray paths in a still further modification of apparatus.

The arrangements of FIG. 5 and FIG. 6 omit the primary reflector of FIGS. 1 to 4 as a separate entity. The function of the primary reflector is assumed to some extent by the minute reflectors as at 98 on the inner surface of the spherical cavity. The typical arrangement, however, is expected to employ a separate primary reflector whose characteristics are suitably matched to the shape of the enclosing configuration defined by the reflective elements thereof, and the desired instrument characteristics. As shown in FIG. 7, the primary reflector may take the form of a hemisphere 34c, or possibly it may take the form of a greater or lesser portion of a sphere or an entire sphere.

Again, other primary reflector shapes in addition to those illustrated and described may be found appropriate, particularly when the cavities are not of hemispherical configuration but assume the shapes of other surfaces of revolution or other shapes. Moreover, while in the typical geometries illustrated and described the primary reflectors have specular surfaces and the cavities have diffusing surfaces, at least for some applications the cavities as at 36 and 40 may have specular surfaces and the primary reflectors 34 may have diffusing surfaces with good results. In this case the radiation reflective elements (surface elements) at the beam directing and/or beam redirecting points simply constitute infinitesimal subdivisions of the continuous specular surface which receive and reflect rays from points on the diffusively reflective surface of the primary reflector.

Figure 8:
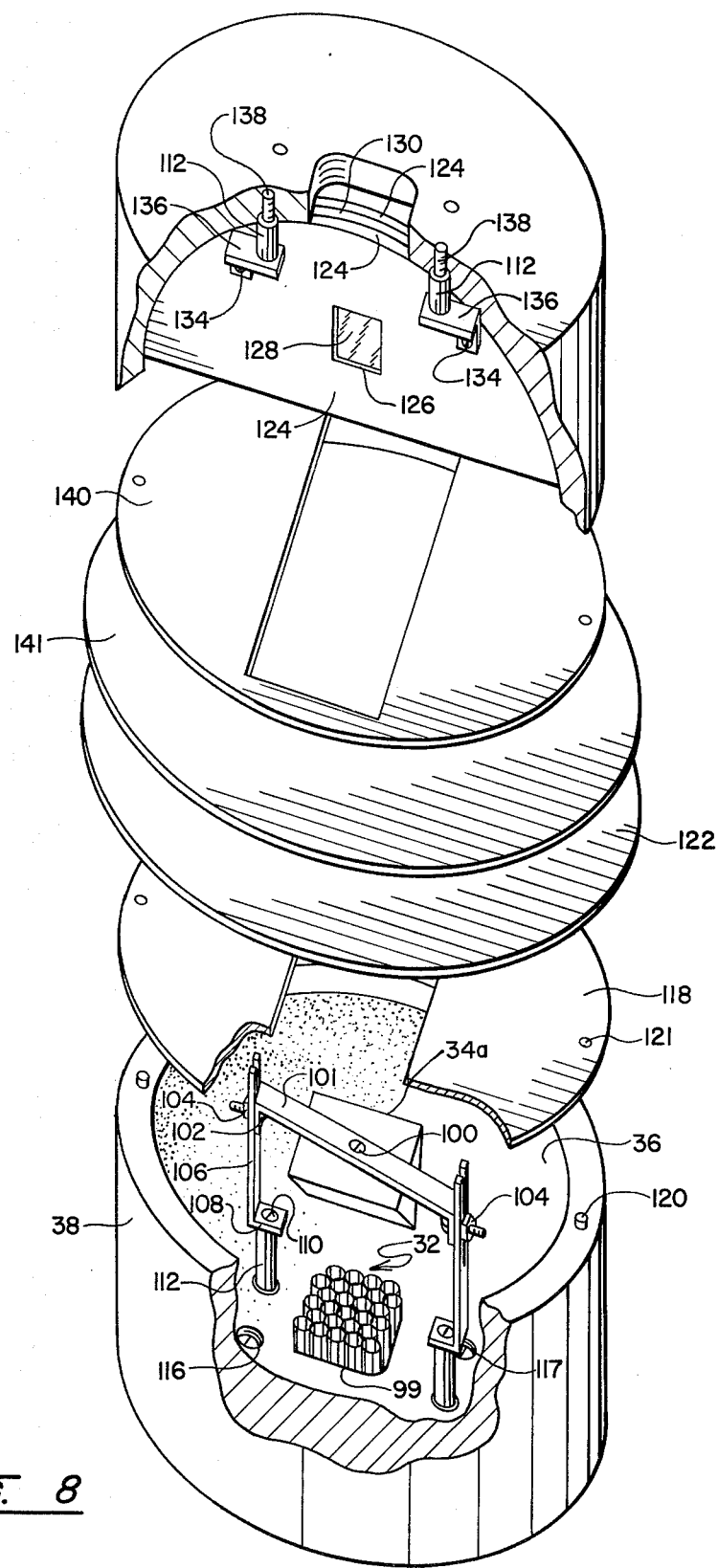
FIG. 8 is an exploded perspective view showing the significant construction details of an apparatus in accordance with the schematic showings of FIG. 2 or FIG. 3.

FIG. 8 shows the significant construction details of one form of the arrangement illustrated schematically in FIGS. 2 and 3. By this construction, an instrument according to this invention was adapted to measure a portion of a film which was viewed instantaneously as an area one inch wide across the width of the film and three inches long in the direction of movement of the film, thereby providing a so-called "streak geometry".

The hemispherical cavities 36 and 40 were three inches in diameter. The collimator 32 was made of an integrally-formed cluster of hexagonally-shaped tubes, which were blackened, with particular care being taken to ensure that the insides of the tubes, especially at the collimator exit end, were finished a dull black. The collimator extended through a generally square opening 99, three-quarters of an inch on a side, along the axis of the one hemisphere 36. The "top" surface of the primary reflector wedge 34a was one inch square, and centrally drilled and tapped to receive a mounting screw 100 for securing the wedge 34a to a cross-bracket 101. The cross-bracket 101 had its ends bent downwardly to form lugs as at 102 which were drilled to accommodate clamping screw and nut assemblies as at 104. The cross-bracket was thereby secured between a pair of stanchions as at 106. Stanchions 106 were slotted vertically so that when the screws were loosened the cross-bracket 101, and thereby the primary reflector wedge 34a, could be adjusted up and down. Experimental results showed that best performance was obtained when the top surface of the wedge was positioned about three-sixteenth of an inch below the plane of the rim of the hemisphere 36. The flat metal stanchions 106 had their bottom ends bent inwardly to form lugs as at 108 which were drilled to accommodate mounting screws as at 110. The lugs 108 were set on tubular spacers as at 112 which were seated in counter-bored openings in the aluminum body which formed the hemisphere. The mounting screws extended through the tubular spacers and into a source housing cover plate 114 so as to secure the hemisphere in its proper position within housing 14 (FIG. 1). Another pair of screws inserted through openings 116 and 117 were used only to help secure the aluminum body of the hemisphere in place and their heads therefore were reset below the surface of the cavity within the counter-bored openings.

In order to better define the area of the film 10 which was to be measured by the instrument, a thin flat aluminum masking plate 118 was fitted over the rim of the hemispherical body and maintained in position with roll pins as at 120 fitting into holes as at 121. Masking plate 118 served to mask off a portion of the area of the film confined by the hemispherical surface of revolution to block the passage of radiation to and from the surface of the film except in a narrow, elongated area thereof. As previously noted, the aperture in masking plate 118 was three inches long in the direction of travel of the film and 1 inch wide in the cross direction. To prevent foreign matter from entering into the assembly, the entire circular opening defined by the rim of the hemisphere 36 was covered by a window 122 of plastic sheet material which was substantially transparent to the infrared radiation wavelengths generated by infrared radiation source 18. Typically window 122 was stretched in drum-head fashion over masking plate 118 and the rim of hemispherical body 38 and retained by conventional means (not shown).

Figure 9:
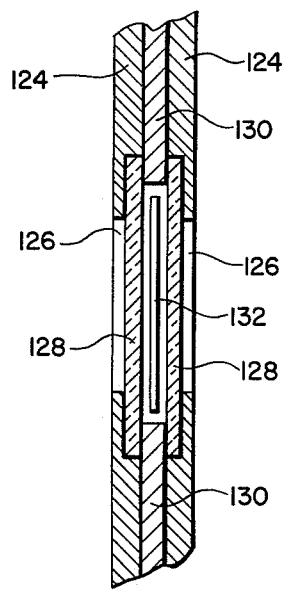
FIG. 9 is a section on the line 9—9 of FIG. 1, showing details of the detector means 44.

Within the other hemispherical body 40 on the opposite side of the sheet, the detector means was assembled as best shown in FIGS. 1, 8 and 9, in the form of a sandwich-like arrangement enclosd between two semicircular aluminum plates 124. Each plate had a square aperture 126 on the outside. Each plate was counter-bored on the inside to form a recess wherein a filter as at 128 was mounted. Sandwiched between the two aluminum plates 124 was a sheet of fiberboard 130 with a mounting aperture to accommodate a radiation detector 132 which was positioned symmetrically along the axis of the hemispherical cavity 40.

Detector 132 was simply cemented in the aperture of the fiberboard support 130. Since the detector aperture 126 was smaller than filters 128, the fiberboard acted as a retainer to hold the filters in place. The stacked assembly of the detector means was held together with screws as at 134, some of which also passed through angle brackets as at 136. The angle brackets were in turn mounted on top of tubular spacers 112 and secured by elongated screws 138 in the same manner as that previously described for mounting the primary reflector in hemispherical body 38 containing the primary reflector and collimator. The hemispherical body 40 containing the detector means was also masked by a masking plate 140 identical with masking plate 118 and the whole was covered with a platic window 141, all in the same manner as previously described for masking plate 118 and window 122.

In order to reduce the amount of undesired scattered and ambient radiation which is allowed to enter the hemispherical cavities, the two masking discs 118 and 140 were blackened on the outside next to windows 122 and 141 and the film 10 being measured. The opposite side (inside) of the masking discs, and the outsides of the two semicircular aluminum plates 124, had polished surfaces, as did the mounting parts, to a reasonable extent. These expedients are believed to significantly increase the efficiency of the source radiation utilization and to help meet as well as possible the criterion that the components of each of the respective radiations at each of the possible phase angles approach equality of intensity as detected by the detecting means.

The instrument to which this invention relates is designed to measure the effects of radiation absorption in the film to the substantial exclusion of errors due to interference effects. The simplest for of interference occurs when one part of a beam of radiation passes through the film whereas another part is reflected from both surfaces, whereupon both the directly transmitted part and the reflected part recombine to form a single beam.

If the reflected part is 180° (or odd multiple thereof) out of phase with the directly transmitted beam, there can be almost completely destructive interference of the emergent beams at the detector, so that the amplitude of the reflected part is effectively subtracted from the amplitude of the transmitted part. If the two parts of the emergent beam are in phase (displaced by 360° or a multiple thereof) there can be almost completely constructive interference where the beam is detected by the detector, so that the amplitudes of the two parts of the beam at the detector are additive. At intermediate phase angles, various degrees of constructive and destructive interference may prevail.

Where components of the radiation can be added at all possible phase angles so that the components at each of the possible phase angles have equal intensity as detected, the interference effect is eliminated. Insofar as the present invention is concerned, considering the velocity of infrared ray propagation, no distinction can be made between a phase angle $\phi$ less than 360° and a greater angle $n$ (360°) + $\phi$ (where $n$ is any integer), since radiations at these phase angles are in phase as detected. At least in some wavelength-film thickness combinations it is apparent that the methods and apparatus of the invention may rely on the addition of a radiation component at 360° + $\phi$, for example, to make the total component detected at the phase angle $\phi$ have an intensity equal to the intensity of components at the other phase angles.

Figure 10:
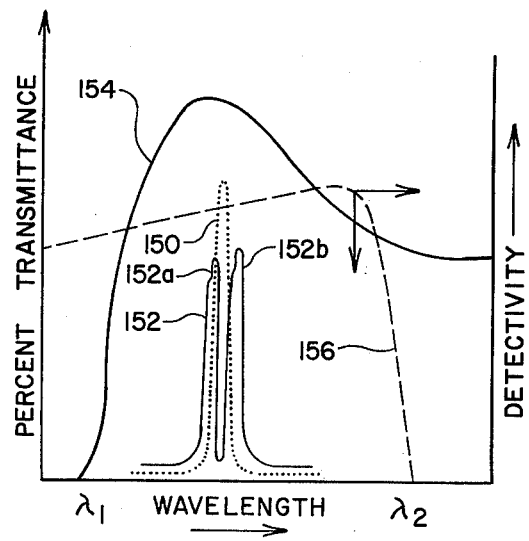
FIG. 10 is a graph of percent transmission and detectivity as a function of wavelength, to illustrate the characteristics of typical filters utilized in an apparatus in accordance with this invention in order to optimize its performance.

In a practical gauging arrangement such as that shown in FIG. 8, structural limitations may not permit the detected components of each radiation to be added at every phase angle, and the components of each of the respective radiations at each of the possible phase angles may not attain absolute equality of intensity as detected by the detecting means, particularly when a considerable range of film thicknesses is involved. However, by following the teachings disclosed herein, it is possible to achieve addition at substantially all possible phase angles and to detect components of the radiations so that the detected components at each of the possible phase angles reasonably approach equality of intensity for practical purposes.

Where less-than-perfect geometrical arrangements such as that depicted in FIG. 8 are to be used for ordinary commercial purposes, many deficiencies of the geometry can be compensated for through the use of the "notched-filter" technique disclosed in U.S. Pat. No. 3,863,071. FIG. 10 illustrates the use of the patented technique in a typical thin film gauging arrangement according to the invention. In FIG. 10, the numeral 150 designates a curve showing the typical transmission characteristics of a filter as at 24 (FIG. 1) which is utilized in generating the one radiation as a narrow band of wavelengths subject to substantial absorption in the film material. The numeral 152 designates a curve showing the typical transmission characteristics of a filter as at 26 which is utilized in generating the other of the first and second radiations as a pair 152a and 152b of narrow bands of wavelengths occupying spectral regions on either side of and closely adjacent to the one narrow band of wavelengths, the radiations having said pair of adjacent wavelengths being substantially less subject to absorption in the film material than the one radiation.

The curve 154 shows the transmission characteristic of the filters 128 (FIGS. 5, 6, 8 and 9) over the detector. The dashed line curve 156 shows the detectivity characteristic of the detector 132. The synergistic action of the filter characteristic 154 and the detectivity characteristic 156 effectively results in a passband from $\lambda_1$ to $\lambda_2$, thereby eliminating the effects of a considerable amount of extraneous radiation from the ambient environment of the instrument.

While the foregoing specification and the drawings describe and illustrate typical methods and apparatus for practicing the invention, it is to be understood that such description and illustration is meant to be illustrative only and not restrictive, since obviously many modifications of the procedures and apparatus described herein can be made without departing from the spirit and scope of the invention.

What is claimed is:

1. A method of measuring a property of an infrared radiation-transmissive film having specular surfaces, comprising the steps of generating first and second infrared radiations having wavelengths selected so that one of the radiations is subject to greater absorption in the film material than the other radiation, directing beams of each of the radiations from a multiplicity of points to a surface of the film at a broad spectrum of incidence angles so that the beams traverse a multiplicity of paths through the film constituting a broad spectrum of path lengths, intercepting radiations leaving the film and redirecting the intercepted radiations from a multiplicity of points to a surface of the film at a broad spectrum of incidence angles so that the redirected radiations also traverse a multiplicity of paths through the film constituting a broad spectrum of path lengths, detecting each of the first and second radiations with detecting means so arranged with respect to the directing and redirecting points that detected components of each radiation are added at substantially all possible phase angles and so that the components of each of the respective radiations at each of the possible phase angles approach equality of intensity as detected by the detecting means and producing a response indicative of the film property as a function of the ratio of the detected intensities of the first and second infrared radiations.

2. A method as in claim 1 wherein a substantial portion of the radiations incident on one surface of the film emerge from the opposite surface, comprising redirecting a major portion of the emergent radiations back to the opposite surface at a broad spectrum of incidence angles.

3. A method as in claim 1 comprising
generating one of the first and second radiations as a narrow band of wavelengths subject to substantial absorption in the film material, and
generating the other of the first and second radiations as a pair of narrow bands of wavelengths occupying spectral regions on either side of and closely adjacent to the narrow band of wavelengths, the radiations having said pair of adjacent wavelengths being substantially less subject to absorption in the film material than said one radiation.

4. A method as in claim 1 comprising locating minute infrared radiation reflective elements at the beam directing points and illuminating the elements by an infrared radiation source which generates the first and second radiations whereby said beams incident on the surface of the film and traversing the paths through the film comprise infrared radiations reflected from the elements.

5. A method as in claim 4 wherein the elements are located in an enclosing configuration which substantially confines a surface area of the film.

6. A method as in claim 5 which comprises directing a primary beam of radiations from the source onto a primary reflector located within the enclosing configuration so that the reflecting elements at the beam directing points are illuminated by infrared radiations reflected from the primary reflector.

7. A method as in claim 6 comprising collimating the primary beam of radiations from the source that are directed onto the primary reflector so that substantially all radiation from the source admitted within the enclosing configuration is reflected by the primary reflector.

8. A method as in claim 5 wherein the enclosing configuration comprises a surface of revolution and wherein the elements are located on the surface of revolution.

9. A method as in claim 8 wherein the surface of revolution is a hemisphere.

10. A method as in claim 8 comprising masking off a portion of the area of the film confined by the surface of revolution to block the passage of radiation to the surface of the film except in a narrow, elongated area thereof.

11. A method as in claim 4 wherein infrared radiation reflective elements are also located at the beam redirecting points.

12. A method as in claim 11 comprising locating radiation reflective elements on both sides of the film to form enclosing configurations which confine an area of the film on both sides thereof.

13. A method as in claim 12 comprising detecting the radiation with a detecting means so arranged that radiation cannot pass from the source to the detecting means without interacting with one of the radiation reflecting elements.

14. A method as in claim 12 wherein each of the enclosing configurations comprises a surface of revolution.

15. A method as in claim 14 wherein each surface of revolution is a hemisphere.

16. A method as in claim 12 which comprises directing a primary beam of radiations from the source through the film from one side thereof to illuminate reflective elements on the opposite side of the film.

17. A method as in claim 4 wherein the beam directing points are located on a continuous material surface, and the radiation reflective elements are formed as an integral portion of the material surface.

18. A method as in claim 17 wherein the continuous material surface is formed of a material which is highly reflective to infrared radiation.

19. A method as in claim 18 wherein the material is aluminum.

20. A method as in claim 19 wherein the radiation reflective elements are formed by sandblasting the surface of the aluminum.

21. Apparatus for measuring a property of an infrared radiation-transmissive film having specular surfaces, comprising
means for generating first and second infrared radiations having wavelengths selected so that one of the radiations is subject to greater absorption in the film material than the other radiation,
means for directing beams of each of the radiations from a multiplicity of points to a surface of the film at a broad spectrum of incidence angles so that the beams traverse a multiplicity of paths through the film constituting a broad spectrum of path lengths,
means for intercepting radiations leaving the film and for redirecting the intercepted radiations from a multiplicity of points to a surface of the film at a broad spectrum of incidence angles so that the redirected radiations also traverse a multiplicity of paths through the film constituting a broad spectrum of path lengths,
means for detecting each of the first and second radiations so that detected components of each radiation are added at substantially all possible phase angles and so that the components of each of the respective radiations at each of the possible phase angles approach equality of intensity as detected, and
means for producing a response indicative of the film property as a function of the ratio of the detected intensities of the first and second infrared radiations.

22. Apparatus as in claim 21 for measuring a film which allows a substantial portion of the radiations incident on one surface of the film to emerge from the opposite surface, comprising means for redirecting a major portion of the emergent radiations back to the opposite surface at a broad spectrum of incidence angles.

23. Apparatus as in claim 21 comprising
means for generating one of the first and second radiations as a narrow band of wavelengths subject to substantial absorption in the film material, and
means for generating the other of the first and second radiations as a pair of narrow bands of wavelengths occupying spectral regions on either side of and closely adjacent to the narrow band of wavelengths, the radiations having said pair of adjacent wavelengths being substantially less subject to absorption in the film material than said one radiation.

24. Apparatus as in claim 21 comprising a multiplicity of minute infrared radiation reflective elements located at the beam directing points,
an infrared radiation source for generating the first and second radiations and
means for illuminating the elements with radiations from the source whereby said beams incident on the surface of the film and traversing the paths through the film comprise infrared radiations reflected from said elements.

25. Apparatus as in claim 24 comprising means for locating the elements in an enclosing configuration which substantially confines a surface area of said film.

26. Apparatus as in claim 25 which comprises
a primary reflector located within the enclosing configuration, and
means for directing a primary beam of radiations from the source onto the primary reflector so that the reflecting elements at the beam-directing points are illuminated by infrared radiations reflected from the primary reflector.

27. Apparatus as in claim 26 comprising means for collimating the primary beam of radiations from the source that are directed onto the primary reflector so that substantially all radiation from the source admitted within the enclosing configuration is reflected by the primary reflector.

28. Apparatus as in claim 25 wherein the enclosing configuration comprises a surface of revolution and wherein the locating means comprises means forming the elements on the surface of revolution.

29. Apparatus as in claim 28 wherein the surface of revolution is a hemisphere.

30. Apparatus as in claim 28 comprising means for masking off a portion of the area of the film confined by the surface of revolution to block the passage of radiation to the surface of the film except in a narrow, elongated area thereof.

31. Apparatus as in claim 24 comprising means for also locating infrared radiation reflective elements at the beam redirecting points.

32. Apparatus as in claim 31 comprising means for locating the radiation reflective elements on both sides of the film to form enclosing configurations which substantially confine an area of the film on both sides thereof.

33. Apparatus as in claim 32 comprising radiation detecting means so arranged that radiation cannot pass from the source to the detecting means without interacting with one of the radiation reflecting elements.

34. Apparatus as in claim 32 wherein each of the enclosing configurations comprises means forming a surface of revolution.

35. Apparatus as in claim 34 wherein each surface of revolution is a hemisphere.

36. Apparatus as in claim 32 comprising means for directing a primary beam of radiations from the source through the film from one side thereof to illuminate reflective elements on the opposite side of the film.

37. Apparatus as in claim 24 wherein the beam-directing points are located on a continuous material surface, comprising means forming the radiation reflective elements as an integral portion of the material surface.

38. Apparatus as in claim 37 wherein the continuous material surface is formed of a material which is highly reflective to infrared radiation.

39. Apparatus as in claim 38 wherein the material is aluminum.

40. Apparatus as in claim 39 wherein the radiation reflective elements comprise sandblasted portions of the aluminum surface.

41. Apparatus for measuring a property of a sheet material, comprising
a radiation source for generating infrared radiation having a wavelength subject to absorption in the sheet material,
means for directing beams of the radiation from a multiplicity of points to a surface of the sheet material at a broad spectrum of incidence angles,
means for intercepting radiation leaving the sheet material and for redirecting the intercepted radiation to a surface of the sheet material,
said directing and redirecting means comprising reflective surface elements forming an enclosing configuration which substantially confines a surface area of the sheet material,
a primary reflector located within the enclosing configuration,
means for directing a primary beam of radiation from the source onto the primary reflector so that the reflective surface elements at the beam-directing points are illuminated by infrared radiation reflected from the primary reflector,
means for detecting a portion of the radiations which have left the sheet material, and
means for producing a response indicative of the sheet property as a function of the detected radiation.

42. Apparatus as in claim 41 for measuring a sheet material which allows a substantial portion of the radiations incident on one surface of the sheet to emerge from the opposite surface, comprising means for redirecting a major portion of the emergent radiations back to the opposite surface.

43. Apparatus as in claim 41 comprising means for collimating the primary beam of radiation from the source that is directed onto the primary reflector so that substantially all radiation from the source admitted within the enclosing configuration is reflected by the primary reflector.

44. Apparatus as in claim 41 wherein the enclosing configuration comprises a surface of revolution and wherein the reflective surface elements are formed on the surface of revolution.

45. Apparatus as in claim 44 wherein the beam directing points are located on a continuous material surface, and wherein the radiation reflective surface elements are formed as an integral portion of the material surface.

46. Apparatus as in claim 45 wherein the continuous material surface is a diffusively reflective surface and wherein the primary reflector has a specular surface.

47. Apparatus as in claim 45 wherein the continuous material surface is a specularly reflective surface and wherein the primary reflector has a diffusively reflective surface.

48. Apparatus as in claim 44 wherein the surface of revolution is a hemisphere.

49. Apparatus as in claim 44 comprising means for masking off a portion of the area of the film confined by the surface of revolution to block the passage of radiation to the surface of the film except in a narrow, elongated area thereof.

50. Apparatus as in claim 41 comprising means for also locating infrared radiation reflective surface elements at the beam redirecting points.

51. Apparatus as in claim 41 comprising means for locating the radiation reflective surface elements on both sides of the film to form enclosing configurations which substantially confine an area of the film on both sides thereof.

52. Apparatus as in claim 51 comprising radiation detecting means so arranged that radiation cannot pass from the source to the detecting means without interacting with one of the radiation reflecting elements.

53. Apparatus as in claim 51 wherein each of the enclosing configurations comprises means forming a surface of revolution.

54. Apparatus as in claim 53 wherein each surface of revolution is a hemisphere.

* * * * *